United States Patent [19]

Handy

[11] Plant 4,530

[45] May 6, 1980

[54] PEAR TREE

[76] Inventor: Glen E. Handy, Rte. 2, Box 347, Troutdale, Oreg. 97060

[21] Appl. No.: 899,691

[22] Filed: Apr. 24, 1978

[51] Int. Cl.[2] ..... A01H 5/00
[52] U.S. Cl. ..... Plt./36
[58] Field of Search ..... Plt./36

[56] References Cited

U.S. PATENT DOCUMENTS

| | | | |
|---|---|---|---|
| P.P. 2,489 | 3/1965 | Scanlon | Plt./36 |
| P.P. 3,193 | 5/1972 | Straw | Plt./36 |
| P.P. 3,815 | 12/1975 | Flemer | Plt./36 |

OTHER PUBLICATIONS

Wyman, Donald *Trees for American Gardens* "General List of Recommended Trees" *Pyrus calleryana,* p. 398.

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

This invention relates to a novel variety of Callery Pear tree, distinguished by its globe shape which is normally apparent two to three years after budding, more vigorous growth rate, green waxy foliage which consistently turns to the same red to red-purple colors each autumn, thornless branches, profuse blooms, with blooms first appearing when the trees are quite young, and its sparse fruit.

4 Drawing Figures

DESCRIPTION

The present invention relates to a new and distinct variety of flowering pear tree of the species botanically known as *Pyrus calleryana* and commonly called "Callery Pear."

My new variety originated from a process of selection performed under my supervision and on cultivated property under my control at Portland, Oreg. More specifically, a number of years ago I grew a large group of approximately thirty thousand of Callery Pear seedlings from seeds which I had purchased. Thereafter, a small number of these seedlings were selected from the large group on the basis of their distinctive characteristics; primarily their more rapid rate of growth. Of these selected seedlings, one in particular, the parent tree of my new variety, exhibited a new and improved combination of characteristics never previously exhibited in any *Pyrus calleryana* trees of which I am aware.

Close observation of the parent tree, asexual reproduction of the parent tree under my direction to produce progeny thereof, and continued observations of such progeny, which possessed identical characteristics to my parent tree so far as observable, and which were subsequently asexually propagated under my direction in Portland, Oreg. by budding, has convinced me that my new tree represents a new and improved variety of *Pyrus calleryana.* Furthermore, these observations have confirmed that my new variety is particularly evidenced by the following unique combination of characteristics which have proven firmly fixed, are outstanding therein, and which distinguish it from all other varieties of this species of which I am aware, including the "Callery" Pear seedling, "Bradford" Pear, "Chanticleer" Pear (U.S. Plant Pat. 2,489) and "Rancho" Pear (U.S. Plant Pat. 2,092):

1. An extremely rapid, vigorous rate of growth;
2. A uniform round or globe-shaped habit of growth which becomes apparent when the budded trees are two to three years old;

3. Waxy leaves;
4. Thornless branches;
5. Leaves which are consistently the same red to red-purple color in the fall; and
6. Exceptionally profuse blooms with blooms first appearing on the trees when they are unusually young.

In determining the above characteristics, I have compared my tree with the "Callery" Pear seedling, "Bradford" Pear, "Chanticleer" Pear and "Rancho" Pear, which were growing under the same conditions in my experimental nursery plot in Portland, Oreg.

The accompanying photographs depict the color of the foliage and flowers of my new variety as nearly true as is reasonably possible to make the same in a color illustration of this character.

FIG. 1 is a color photograph of an entire tree of the present invention taken in later June 1977 to show the globe shape of the tree;

FIG. 2 is a color photograph of leaves of a tree of my variety, taken at the same time as the photograph of FIG. 1, to show their waxy appearance;

FIG. 3 is a color photograph of leaves of my new variety taken in late November 1977 to show their autumn coloration; and FIG. 4 is a color photograph of flowers of the tree of my invention taken in later March 1978.

The primary distinguishing feature of my new tree over other trees of this species is its uniform round or globe shape. This unique habit of growth normally becomes apparent in my trees two to three years after they have been budded. That is, a two to three year old budded tree of my variety shows definite indications of becoming globe shaped. Although at this age such trees are not completely and perfectly round in habit, close observations of my variety have revealed that my tree forms its globe shape early in its life without exception and within three to five years is obviously globular. These observations were made both of the parent tree on its own roots and on asexually reproduced progeny. None of the observed trees were pruned except that, as typical of other varieties including the "Bradford" Pear, one year whips are typically cut back to encourage the tree to branch during its second year from budding. In contrast, seedling Callery Pear trees exhibit an irregular growth habit and do not have this ornamental globe shape form. I have also observed this irregular habit in "Bradford" Pear trees. By irregular growth habit, I mean that these trees have a non-uniform shape. That is, the shape varies between individual trees of the same variety. However, in general, "Callery" Pear seedlings are a small bushy looking tree and "Bradford" Pear trees are semi-pyramidal, slender and upright branching. Also, "Chanticleer" Pear trees assume a conical shape and "Rancho" Pear trees are pyramidal with a broad base. Thus, none of these varieties have been observed to have the early appearing round-headed globular shape of my tree.

In addition, trees of my new variety, particularly when they are young, exhibit a much more vigorous rate of growth than known Callery Pear trees. More specifically, in some early observations of young trees of my variety, it was noticed that they were taller than other trees of this species of the same age which were growing in the same area. In fact, some of these young trees of my new variety were observed to be about fifty percent taller than these other trees. In particular, the growth of my parent tree was compared with that of "Callery" Pear seedlings and of "Bradford" Pear trees. In addition, the growth of progeny of my parent tree was compared annually over a seven year period with the growth of these two varieties and also with the growth of the "Chanticleer" and "Rancho" Pear trees. These comparisons were made by visual observations and measurements. From my observations, the following typical heights were apparent:

| Age of Tree | New Variety | "Bradford" Pear | Callery Seedling | "Chanticleer" Pear | "Rancho" Pear |
|---|---|---|---|---|---|
| 1 yr. | 7–8′ | 6′ | 4–5′ | 7–8′ | 6–7′ |
| 2 yr. | 8–10′ | 7–8′ | 5–6′ | 8–10′ | 7–8′ |
| 3 yr. | 10–12′ | 8–10′ | 7–8′ | 10–12′ | 9–10′ |
| Annual growth thereafter except for year following transplanting: | | | | | |
| | 8–10″ | 6–8″, | 4–6″ | 9–12″ | 8–10″ |

These trees are normally transplanted after their third year and consequently grow very little for one year after transplanting.

As mentioned previously, the foliage of my tree has a green waxy lustrous appearance. In comparison, seedling Callery Pear trees have a dull, non-waxy appearing leaf. In addition, the leaves of my tree, particularly those on new growth branches, are not as round as leaves of seedling "Callery"Pear trees. In contrast to my tree, the leaves of the "Bradford" Pear tree are not as glossy as the leaves of my new tree. Also, the leaves of the "Bradford" Pear tree are approximately 3–4 cm. shorter and slightly broader than the leaves of my new variety. Furthermore, unlike my new variety, the underside of "Bradford" Pear tree leaves are tomentose. Both the "Rancho" Pear and "Chanticleer" Pear have a glossy leaf. However, the "Chanticleer" Pear leaf is narrower than the leaf of my tree while the "Rancho" Pear leaf is more rounded.

The trees of my new variety turn consistently to the same fall colors. That is, each autumn the foliage of my tree turns the same brilliant red to red-purple colors. I am convinced that this is due because my tree consistently becomes dormant and the leaves attain their fall color before winter weather arrives. In contrast, other Callery Pears have inconsistent fall colors. For example, one fall, Callery Pear seedlings may have red foliage, and the next fall, the foliage may be a mixture of reds and yellow. In addition, both "Bradford" Pear and "Chanticleer" Pear trees grow late in the growing season in our area. Consequently, early winter weather sometimes occurs before these trees have become dormant and before their leaves have taken on their fall colors. Thus, the fall colors of these varieties are not the same from season to season, but, depend in large part upon the weather. Although the "Rancho" Pear tree has more consistent fall leaf color than the "Bradford" and "Chanticleer" trees, it is still somewhat dependent upon the growing season.

In contrast to the thornlessness of my new variety, "Callery" Pear seedlings are extremely thorny. In addition, occasional individual trees of both the "Bradford" and "Rancho" Pear varieties have been observed by me to have thorns. On the other hand, the "Chanticleer" Pear is also thornless.

Visual observations have revealed that my new variety blooms profusely with the blooms normally occurring early in April. In addition, it is not unusual for trees of my variety to begin flowering when they are two years old. On the other hand, visual observations have revealed that other trees of the species do not flower as profusely and typically do not begin to flower until their fifth year.

Moreover, my Callery Pear trees produce little or no fruit and the fruit that is produced is small and hard. Like the "Bradford" Pear tree, my new variety is self-unfruitful and cross-fruitful. However, the fruit of my tree appears smaller than that of the "Bradford" Pear. In comparison, seedling Callery Pear trees produce prolific amounts of fruit. This difference makes seedling trees of this species less desirable than my new variety because of the greater mess that results when their fruit drops.

Otherwise, insofar as I've been able to observe at this time, my new variety is generally typical of the species.

Also, my variety is generally disease free and hardier than the "Bradford" Pear tree. This hardiness results from my new variety becoming dormant before winter weather sets in. Typically, in Oreg., my tree becomes dormant sometime between the 15th and 25th of September. In contrast, the "Bradford" Pear usually becomes dormant about two weeks later and for this reason is often still growing when this weather strikes. Consequently, the "Bradford" Pear is more subject to winter kill than my new variety.

The following is a detailed description of my new variety of *Pyrus calleryana* tree, with color terminology in accordance with the Royal Horticultural Society Color Chart (hereinafter RHS), published by the Royal Horticultural Society of London. It is pointed out, however, that the coloration of the leaves as indicated below is only approximate because the coloration varies considerably depending upon lighting conditions and time of year. In addition, the size and shape of the leaves varies depending upon the nature of the growing season.

Parentage: A seedling selected from a large group of approximately thirty thousand *Pyrus calleryana* seedlings.

Propagation: Holds to distinguishing characteristics through succeeding propagation by budding on *Pyrus calleryana* understock.

Locality where grown and observed: Portland, Oreg.

Tree: Upright, healthy, rapid growing; uniform globe shape which becomes apparent when the trees are two to three years old.

Foliage:

*Shape.*—Ovate, with some leaves being broader than others.

*Apex.*—Acuminate.

*Base.*—Obtuse.

*Margin.*—Crenate.

*Size.*—Typically twelve cm long and six cm broad.

*Color.*—In early summer the immature leaves are a waxy green color like RHS plate 144A and the mature leaves are a darker waxy green color like RHS plate 137A. In the fall, the leaves are a red to red-purple color like RHS plate 183A to a deep red-purple color somewhat deeper than RHS plate 187A.

Flowers:

*Cluster.*—Corymb.

*Petals.*—Five.

*Styles.*—Two.

*Anthers.*—A violet color like RHS plate 187D.

*Size.*—Typically 1.5 cm to 2 cm in diameter.

I claim:

1. A new and distinct variety of flowering pear tree substantially as herein shown and described, characterized particularly as to novelty by a globe shaped form which is normally apparent when the tree is two to three years old, a vigorous rate of growth, thornless branched, waxy foliage, which turns consistently a red to red-purple color in the fall, profuse blooms which begin appearing when the tree is extremely young, and sparse fruit production.

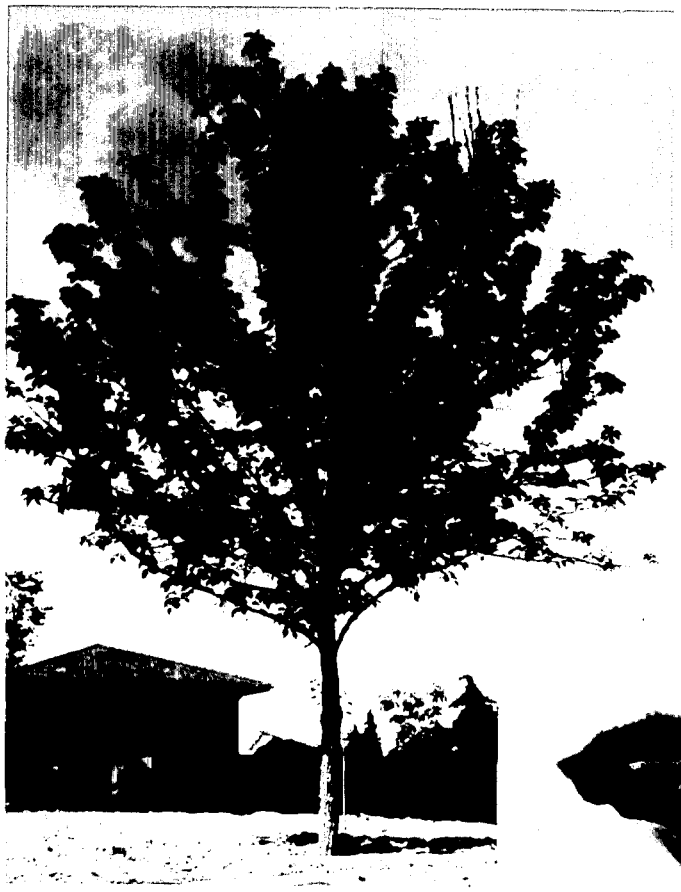
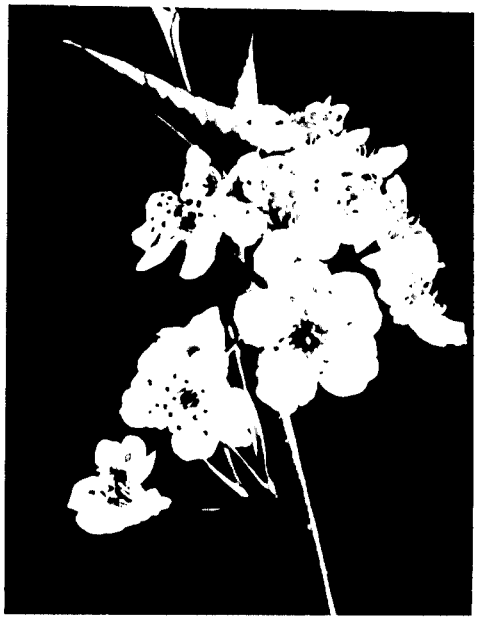
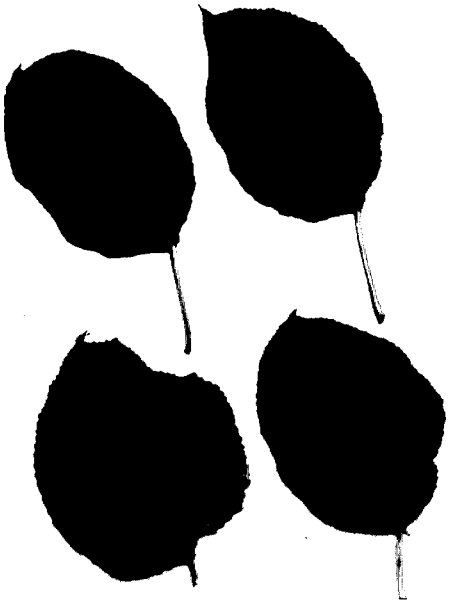
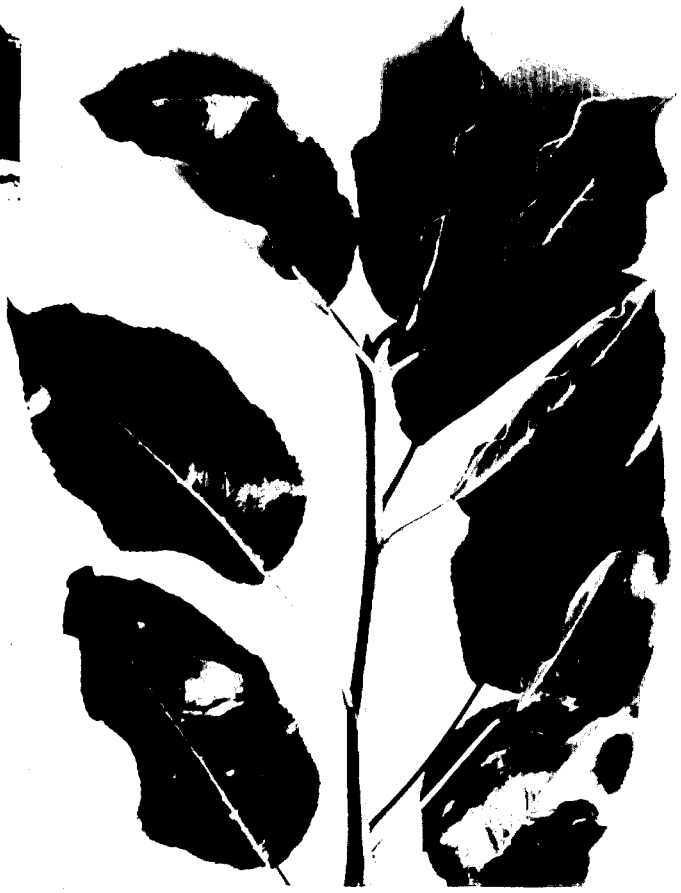

* * * * *